United States Patent
Campbell et al.

(10) Patent No.: US 10,332,622 B2
(45) Date of Patent: Jun. 25, 2019

(54) METHOD, APPARATUS, AND COMPUTER PROGRAM PRODUCT FOR FACILITATING QUERY INITIATION AND QUERY RESPONSE

(71) Applicant: Hyland Software, Inc., Westlake, OH (US)

(72) Inventors: Brian Campbell, Cumming, GA (US); Charles Steven Grundy, Roswell, GA (US); Timothy J Shippy, Sandy Springs, GA (US)

(73) Assignee: HYLAND SOFTWARE, INC., Westlake, OH (US)

( * ) Notice: Subject to any disclaimer, the term of this patent is extended or adjusted under 35 U.S.C. 154(b) by 1173 days.

(21) Appl. No.: 14/616,954

(22) Filed: Feb. 9, 2015

(65) Prior Publication Data
US 2016/0232298 A1 Aug. 11, 2016

(51) Int. Cl.
*G06Q 50/22* (2018.01)
*G16H 10/60* (2018.01)

(52) U.S. Cl.
CPC .............. *G16H 10/60* (2018.01); *G06Q 50/22* (2013.01)

(58) Field of Classification Search
CPC .......... G06Q 50/22; G06Q 50/24; G16H 10/60
USPC .......................................................... 705/2–3
See application file for complete search history.

(56) References Cited

U.S. PATENT DOCUMENTS

| | | | | |
|---|---|---|---|---|
| 2009/0138287 A1* | 5/2009 | Hermann, Jr. | ......... | G06Q 50/22 705/3 |
| 2010/0179852 A1* | 7/2010 | Tomizuka | .............. | G06Q 10/00 705/3 |

* cited by examiner

*Primary Examiner* — Joy Chng
(74) *Attorney, Agent, or Firm* — Medley, Behrens & Lewis, LLC

(57) ABSTRACT

A method, apparatus, and computer program product are provided for facilitating query initiation and query response. Form-based templates may be configured to include data extracted from an electronic health record (EHR). Additional fields may be configured such that a query initiator provides input to the fields and/or links a document. The query initiator may select the intended query responder. The query is assigned to the responder such that the responder may access the query in a queue. The query responder may provide input to required and/or optional fields. Completed queries may be stored in the EHR of the associated patient.

20 Claims, 5 Drawing Sheets

Figure 5

METHOD, APPARATUS, AND COMPUTER PROGRAM PRODUCT FOR FACILITATING QUERY INITIATION AND QUERY RESPONSE

TECHNOLOGICAL FIELD

Example embodiments of the present invention relate generally to computer technology and, more particularly, to methods, apparatuses, and computer program products for facilitating query initiation and query response.

BACKGROUND

The widespread use of modern computing technology has led to an increasing amount of electronic information. The healthcare industry, among others, is one that aims to improve the organization and maintenance of the electronic information while providing secure and efficient access to various authorized users. Electronic health records (EHRs) stored on a health information system (HIS) may be updated and accessed by many users having different roles.

For example, medical coders may review EHRs to identify pertinent information regarding an encounter (e.g., a patient visit to a medical facility). The medical coders may then identify the correct billing code based on the information in the EHR, so that an accurate claim or bill is generated based on the services provided. In some examples, the medical coder may need additional information not available in the EHR or clarification of the data that is available.

BRIEF SUMMARY OF SOME EXAMPLE EMBODIMENTS

Methods, apparatuses, and computer program products are therefore provided for facilitating query initiation and query response. According to embodiments provided herein, a user, such as a medical coder may request additional information from another user, such as a physician. The initiator of the query may select a preconfigured form based template to be used in generating the query. Context data, such as that relating to the patient (e.g., name, age, gender, etc.) and/or encounter (e.g., visit date, facility, etc.) may be extracted from the EHR and applied to the template. The query may then be provided to the responder (e.g., physician) so that the additional information may be completed and provided to the initiator.

A method is provided for facilitating query initiation and query response. In some embodiments, the method includes receiving an indication of a selection of a form-based template for generating the query and receiving an indication of a query responder identifying the responder for which the query is intended. In some examples, the method includes receiving a query initiator input to be included in the query and identifying context data associated with an electronic health record and based on the selected form-based query template. The method further includes storing the query initiator input in association with the selected form based template and the context data associated with the electronic health record, and causing provision of the query to the query responder such that the query initiator input and the context data associated with the electronic health record are provided in the query.

In some examples, the method includes receiving query responder input from the query responder, and storing a completed query in association with the electronic health record. The method further includes receiving an indication of a plurality of query responder input fields and respective requirement indicators. In an instance there are no required query responder input fields, the method includes enforcing at least one query responder input to be made to complete the query. In an instance there are required query responder input fields, the method includes enforcing all the required query responder input fields to be provided to complete the query.

In some embodiments, the method includes receiving an indication to redirect the query to a different query responder, and causing the query to be provided to the different query responder. In some examples, the method includes receiving another form-based query template, and receiving a plurality of query initiator fields and a plurality of query responder fields. Each of the query initiator fields and query responder fields are configured as optional or required.

The method further includes receiving an indication from the query initiator to link a document to the query, and in response to the indication from the query initiator to link the document to the query, causing the document to be provided to the query responder.

An apparatus is provided for facilitating query initiation and query response. The apparatus includes processing circuitry configured to cause the apparatus to perform at least receiving an indication of a selection of a form-based template for generating the query and receiving an indication of a query responder identifying the responder for which the query is intended. The processing circuitry is further configured to cause the apparatus to receive a query initiator input to be included in the query, and identify context data associated with an electronic health record and based on the selected form-based query template. The processing circuitry is further configured to cause the apparatus to perform storing the query initiator input in association with the selected form based template and the context data associated with the electronic health record, and causing provision of the query to the query responder such that the query initiator input and the context data associated with the electronic health record are provided in the query.

In some examples, the processing circuitry is further configured to cause the apparatus to perform at least receiving query responder input from the query responder, and storing a completed query in association with the electronic health record. In some examples, the processing circuitry is further configured for receiving an indication of a plurality of query responder input fields and respective requirement indicators. In an instance there are no required query responder input fields, the processing circuitry causes the apparatus to enforce at least one query responder input to be made to complete the query. In an instance there are required query responder input fields, the processing circuitry causes the apparatus to enforce all the required query responder input fields to be provided to complete the query.

In some examples, the processing circuitry is further configured to cause the apparatus to receive an indication to redirect the query to a different query responder, and cause the query to be provided to the different query responder. The apparatus may be further configured by processing circuitry to receive another form-based query template, and to receive a plurality of query initiator fields and a plurality of query responder fields, wherein each of the query initiator fields and query responder fields are configured as optional or required.

In some embodiments, the processing circuitry is further configured to cause the apparatus to receive an indication from the query initiator to link a document to the query. In response to the indication from the query initiator to link the document to the query, the processing circuitry may be configured to cause the document to be provided to the query responder.

A computer program product is provided for facilitating query initiation and query response. The computer program product comprises at least one non-transitory computer-readable medium having computer-readable program instructions stored therein, with the computer-readable program instructions comprising instructions, which when performed by an apparatus, are configured to cause the apparatus to receive an indication of a selection of a form-based template for generating the query and receiving an indication of a query responder identifying the responder for which the query is intended.

In some embodiments, the computer-readable program instructions further comprise instructions for receiving a query initiator input to be included in the query, identifying context data associated with an electronic health record and based on the selected form-based query template, and storing the query initiator input in association with the selected form based template and the context data associated with the electronic health record. The query is then provided to the query responder such that the query initiator input and the context data associated with the electronic health record are provided in the query.

In some embodiments, the computer program product causes the apparatus to receive query responder input from the query responder, and store a completed query in association with the electronic health record. In some examples, the computer-readable program instructions further comprise instructions to cause the apparatus to perform at least receiving an indication of a plurality of query responder input fields and respective requirement indicators. In an instance there are no required query responder input fields, the computer program product causes the apparatus to enforce at least one query responder input to be made to complete the query. In an instance there are required query responder input fields, the computer program product causes the apparatus to enforce all the required query responder input fields to be provided to complete the query.

In some embodiments, the computer-readable program instructions further comprise instructions to cause the apparatus to perform at least receiving an indication to redirect the query to a different query responder, and causing the query to be provided to the different query responder. In some examples, the computer-readable program instructions further comprise instructions to cause the apparatus to receive another form-based query template, and receive a plurality of query initiator fields and a plurality of query responder fields. Each of the query initiator fields and query responder fields are configured as optional or required.

In some embodiments, the computer-readable program instructions further comprise instructions to cause the apparatus to perform receiving an indication from the query initiator to link a document to the query, and in response to the indication from the query initiator to link the document to the query, causing the document to be provided to the query responder.

An apparatus is provided for facilitating query initiation and query response. The apparatus comprises means for receiving an indication of a selection of a form-based template for generating the query and means for receiving an indication of a query responder identifying the responder for which the query is intended. The apparatus further includes means for receiving a query initiator input to be included in the query, means for identifying context data associated with an electronic health record and based on the selected form-based query template, and means for storing the query initiator input in association with the selected form based template and the context data associated with the electronic health record. The apparatus includes means for providing the query to the query responder such that the query initiator input and the context data associated with the electronic health record are provided in the query.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
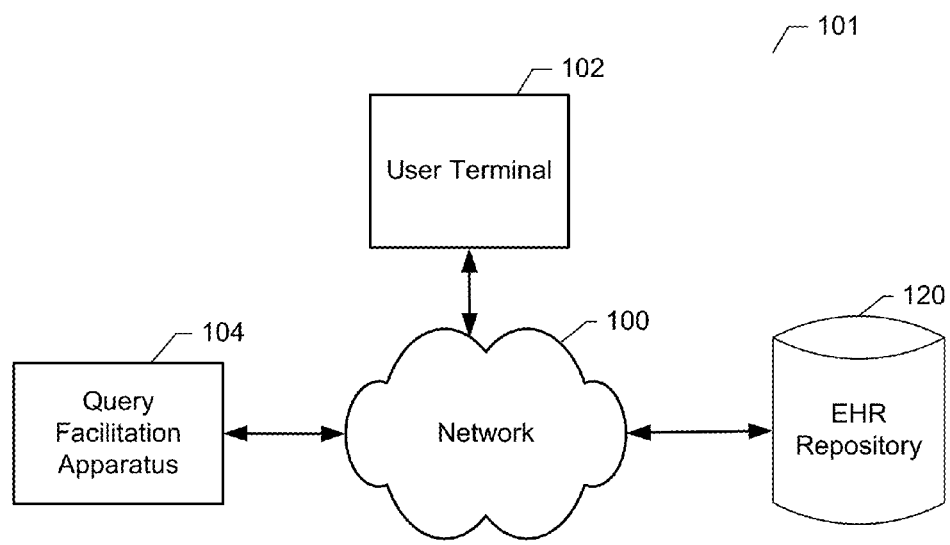
Figure 2:
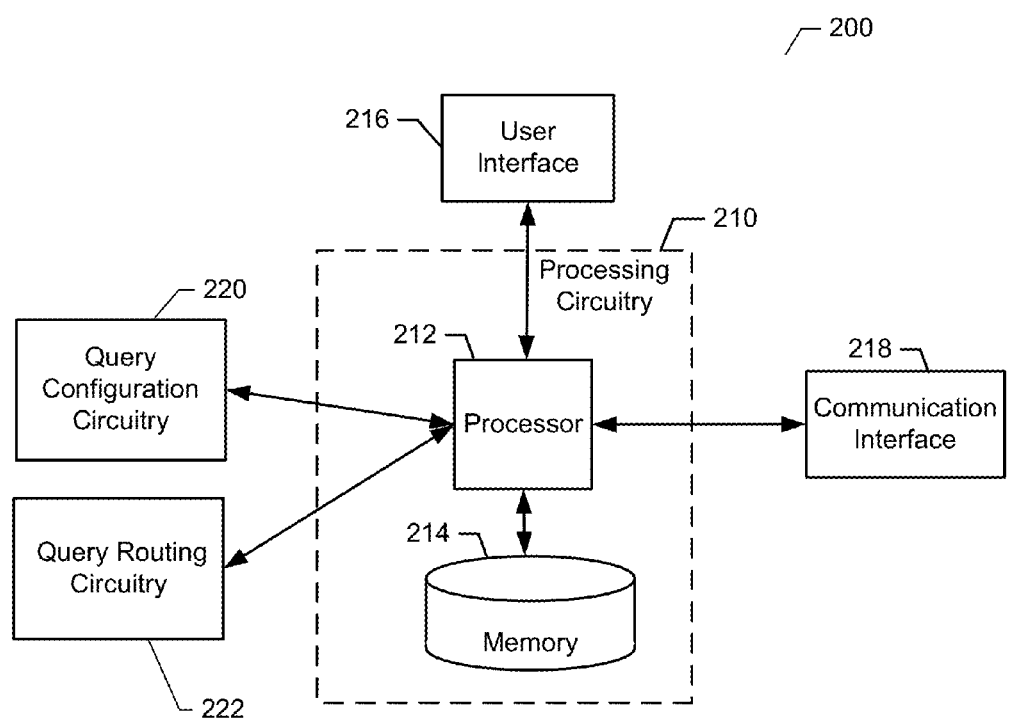
Figure 3:
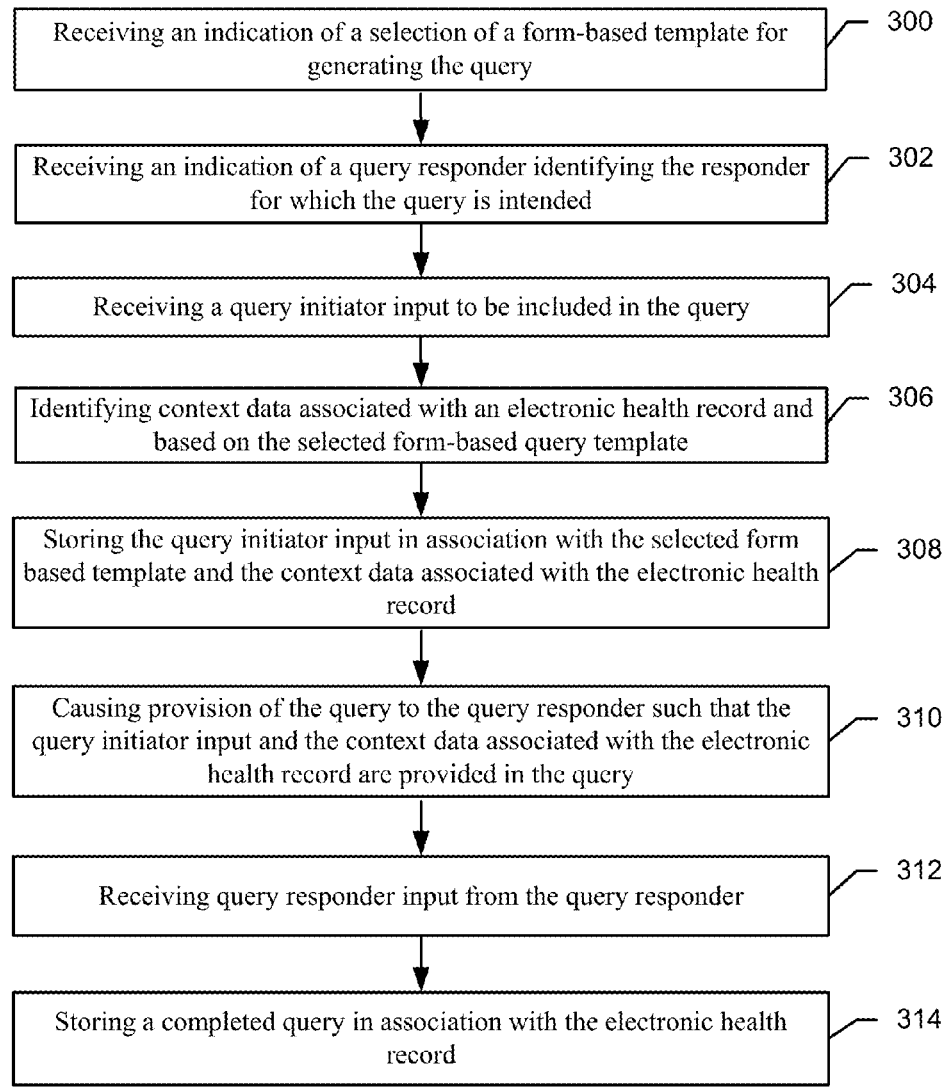
Figure 4:
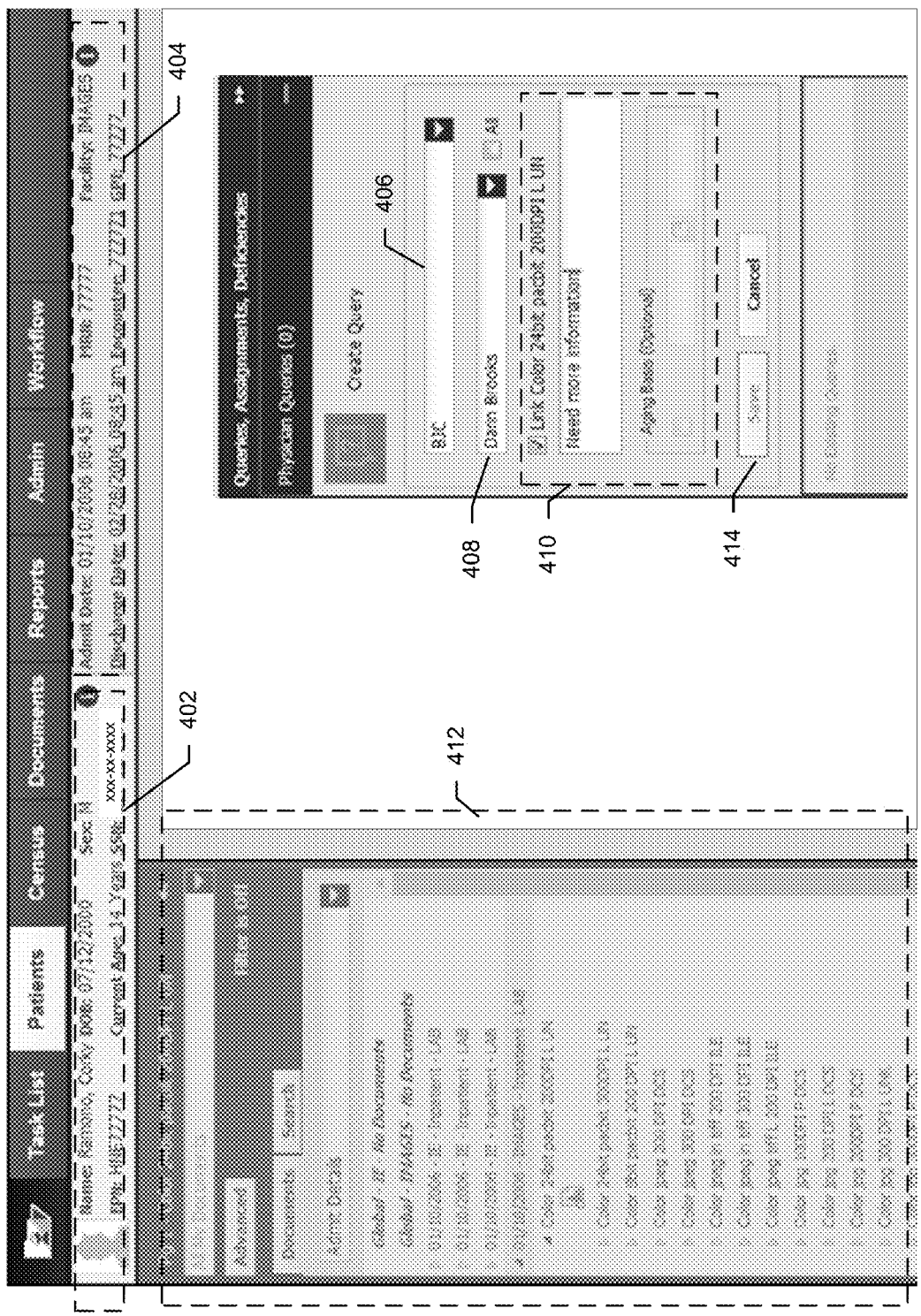
Figure 6:

Having thus described embodiments of the invention in general terms, reference will now be made to the accompanying drawings, which are not necessarily drawn to scale, and wherein:

FIG. 1 is a block diagram of a HIS for facilitating query initiation and query response, according to some example embodiments;

FIG. 2 is a block diagram of an apparatus for facilitating query initiation and query response, according to some example embodiments;

FIG. 3 is a flowchart of operations for facilitating query initiation and query response, according to some example embodiments; and FIGS. 4-6 are example user interfaces for facilitating query initiation and query response, according to some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to another computing device, it will be appreciated that the data may be sent directly to the other computing device or may be sent to the other computing device via one or more interlinking computing devices, such as, for example, one or more servers, relays, routers, network access points, and/or the like.

As introduced above, medical coders may require additional information or clarification from physicians or other healthcare practitioner before coding medical services for billing and/or claim submission purposes. Alternative methods, such as emailing, messaging, and/or faxing particular questions to a physician may be inefficient, prone to errors, and may result in redundant data and/or documents stored on a HIS. Multiple inquiries and follow-up communications due to slow response times may require significant usage of memory on a HIS.

Furthermore, requests to the physician may in some instances be overlooked. Once a request is received by a physician, the physician may need to manually retrieve an EHR and review pertinent information, such as a date of an encounter to recall the details requested. Furthermore, the process relies on the requestor to ensure any documentation is added to the associated EHR. In some instances this may require printing and scanning of documents, and/or uploading a document such that it is associated with a correct EHR. A mistyped patient identifier and/or the like may result in the document being linked to the incorrect EHR.

Various other third party solutions may be limited with regard to customization and integration with existing health information systems and EHR data repositories. Special practices and/or medical facilities may require specific fields or information to be included in queries. Limited system integration may require requestors to manually provide pertinent data in or with the query, while in some examples the responder may have to search for the information.

Example embodiments provided herein provide for customization of form-based templates to be used as queries from an initiator to responder. A form-based template may be created with software such as FormFast®, Adobe®, and/or the like. A user may therefore create and/or upload a form to be used as a query template. A form-based template may be configured to include specific fields to be prefilled with data such as from an EHR, and/or provided as inputs such that users may provide input to the fields. In this regard, some fields may be designated for specific user or user roles (e.g., query initiator and/or query responder). Fields may also be flagged as required or optional.

A form-based template may therefore be configured for specific scenarios and re-used accordingly. As described herein, a medical coder may utilize a form-based template to generate a query for a physician or other query responder. A form-based template may therefore be selected by a query initiator based on a specific scenario, such as an encounter type, facility, and/or the like. The query initiator may ask specific questions of the query responder (e.g., physician), such as by free form text. The query initiator may link documents to the query for efficient retrieval. The query initiator may select a specific query responder such that the query is directed to the appropriate individual or group.

Once the query initiator saves or submits the query, a reference to the form-based template, along with data provided as query initiator inputs to the form for a particular scenario, may be mapped to an EHR. Therefore, when the query responder retrieves the query, such as from a task or work queue, the data from the EHR and/or query initiator input is loaded into the form in the correct fields. The query responder can then review the query as well as pertinent EHR data in a streamlined document. Example embodiments are described in further detail herein.

The health care industry is an example industry that may benefit from embodiments provided herein. As introduced above and described in further detail herein, medical coders may query physicians or other medical practitioners so the medical coders have adequate information to apply appropriate codes for billing and insurance purposes.

While the healthcare industry is referred to throughout as an example industry that may benefit from the facilitation of query initiation and query response, it will be appreciated that embodiments provided herein may be applied to and implemented in systems configured to manage documents relating to any type of industry.

FIG. 1 illustrates a HIS 101 for providing facilitation of query initiation and query response according to some example embodiments. It will be appreciated that the HIS 101, as well as the illustrations in other figures, are each provided as an example of an embodiment(s) and should not be construed to narrow the scope or spirit of the disclosure in any way. In this regard, the scope of the disclosure encompasses many potential embodiments in addition to those illustrated and described herein. As such, while FIG. 1 illustrates one example of a configuration of a system, numerous other configurations may also be used to implement embodiments of the present invention.

In general, HIS 101 includes a user terminal 102 to enable users such as query initiators and query responders to interact with the query facilitation apparatus 104 over network 100. EHR repository 120 may optionally provide additional information regarding EHR to the query facilitation apparatus 104 and/or user terminal 102, and may be configured to store queries according to example embodiments.

In general, the user terminal 102 may be configured to access user interface displays provided by the query facilitation apparatus 104. Query initiators and query responders may both use respective user terminals 102 to initiate and respond to queries. In this regard, the query initiator may initiate a query from a user terminal 102 that is remote from a user terminal 102 by which the query responder responds to the query. The user terminal 102 may be embodied by a wide variety of devices including mobile terminals, personal computers, work stations, personal digital assistants (PDAs), pagers, mobile telephones, or any combination of the aforementioned.

The query facilitation apparatus 104 provides for configuration of form-based query templates and the routing of queries between initiators and responders. The query facilitation apparatus 104 may be embodied as or comprised by a computing device. In some example embodiments, query facilitation apparatus 104 may be implemented as a distributed system or a cloud based entity that may be implemented within network 100. In this regard, query facilitation apparatus 104 may comprise one or more servers, a server cluster, one or more network nodes, a cloud computing infrastructure, some combination thereof, or the like. The query facilitation apparatus 104 is described in further detail with respect to FIG. 2 below.

The EHR repository 120 may be any database, server, third party system, data warehouse, or the like configured to store EHRs, such as but not limited to patient records, encounter records, lab results, surgery reports, and/or the like. The EHR repository 120 may, for example, be operative within a hospital or other medical facility network for consolidating EHRs. In some examples, the EHR repository 120 may be embodied as a laptop computer, tablet computer, mobile phone, desktop computer, workstation, or other like computing device.

Network 100 may be embodied in a local area network, the Internet, any other form of a network, or in any combination thereof, including proprietary private and semi-private networks and public networks. The network 100 may comprise a wired network, wireless network (e.g., a cellular network, wireless local area network, wireless wide area network, some combination thereof, or the like), or a combination thereof, and in some example embodiments comprises at least a portion of the Internet.

FIG. 2 illustrates an example apparatus 200 that may implement a query facilitation apparatus 104, in accordance with some example embodiments. However, it should be noted that the components, devices, and elements illustrated in and described with respect to FIG. 2 below may not be mandatory and thus some may be omitted in certain embodiments. Additionally, some embodiments may include further or different components, devices, or elements beyond those illustrated in and described with respect to FIG. 2.

Processing circuitry 210 may be configured to perform actions in accordance with one or more example embodiments disclosed herein. In this regard, the processing circuitry 210 may be configured to perform and/or control performance of one or more functionalities of the query facilitation apparatus 104, in accordance with various example embodiments. The processing circuitry 210 may be configured to perform data processing, application execution, and/or other processing and management services according to one or more example embodiments. In some embodiments, query facilitation apparatus 104, or a portion(s) or component(s) thereof, such as the processing circuitry 210, may be embodied or comprised as a computing device, e.g., an integrated circuit or other circuitry. The circuitry may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, communication interface 218, query configuration circuitry 220, and/or query routing circuitry 222. As such, the processing circuitry 210 may be embodied as a circuit chip (e.g., an integrated circuit) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of the query facilitation apparatus 104 as described herein. The plurality of processors may be embodied on a single computing device or distributed across a plurality of computing devices collectively configured to function as query facilitation apparatus 104. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

The query configuration circuitry 220 and/or query routing circuitry 222 may include respective and/or shared hardware configured to perform functions as described hereinafter, and communicate with respective circuitry and components of apparatus 200 via a network interface. Query configuration circuitry 220 and/or query routing circuitry 222 may utilize processing circuitry, such as the processor 212, to perform such actions. However, it should also be appreciated that, in some embodiments, any of the circuitry 220 and/or 222 may include a separate processor, specially configured field programmable gate array (FPGA), or application specific interface circuit (ASIC) to perform various respective functions, described in further details hereinafter. Circuitry 220 and/or 222 is therefore implemented using hardware components of the apparatus configured by either hardware or software for implementing these functions.

In general, the query configuration circuitry 220 may comprise hardware and/or software configured to enable users to upload form-based templates to be configured as query templates. The query configuration circuitry 220 may be further configured to receive user input to apply to the form-based template to facilitate the initiation and completion of queries.

In general, the query routing circuitry 222 may comprise hardware and/or software configured to assign queries to query responders, notify query initiators of completion, and track query statuses. The query routing circuitry 222 may maintain query statuses based on the stage of the query initiation and responding processes. The query routing circuitry 222 may be configured to set a query status to incomplete upon creation, and assign the query to a task list of the assigned query responded, as may be designated by the query initiator. Upon receiving a response from the query responder, the query routing circuitry 222 may update the query status to complete, and assign the query to a task list of the query initiator such that the query initiator may view the response and complete the associated task for which the additional information is needed.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices collectively configured to function as query facilitation apparatus 104. The memory 214 may be configured to store information, data, applications, instructions and/or the like for enabling query facilitation apparatus 104 to carry out various functions in accordance with one or more example embodiments. For example, the memory 214 may be configured to buffer input data for processing by the processor 212. Additionally or alternatively, the memory 214 may be configured to store instructions for execution by the processor 212. As yet another alternative, the memory 214 may include one or more databases that may store a variety of files, contents, or data sets. Among the contents of the memory 214, applications may be stored for execution by the processor 212 to carry out the functionality associated with each respective application. In some cases, the memory 214 may be in communication with one or more of the processor 212, user interface 216, communication interface 218, query configuration circuitry 220, and/or query routing circuitry 222 for passing information among components of client system query facilitation apparatus 104. In some examples, memory 214 may include EHR repository 120.

The user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a joystick, a display, a touch screen display, a microphone, a speaker, and/or other input/output mechanisms. As such, the user interface 216 may, in some example embodiments, provide means for user control of managing or processing data access operations and/or the like. In some examples, user interface 216 may not be present on query facilitation apparatus 104, but may be present on user terminal 102 and may be configured to provide displays generated by query facilitation apparatus 104 to a user as described herein. Accordingly, regardless of implementation, the user interface 216 may provide input and output means in accordance with one or more example embodiments.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication between components of HIS 101 via network 100. Accordingly, the communication interface 218 may, for example, include supporting hardware and/or software for enabling wireless and/or wired communications via cable, digital subscriber line (DSL), universal serial bus (USB), Ethernet, or other methods.

FIG. 3 is a flowchart illustrating example operations of the query facilitation apparatus 104 according to an example embodiment. As shown by operation 300, the query facilitation apparatus 104 may include means, such as user interface 216, communication interface 218, query configuration circuitry 220, processing circuitry 210 and/or the like, for receiving an indication of a selection of a form-based template for generating the query. In this regard, the query initiator, such as a medical biller, may select a preconfigured form-based template from a list of available templates or may create a new form-based template.

FIG. 4 is an example user interface that may be generated by query facilitation apparatus 104 for display on user terminal 102, for example. The user interface of FIG. 4 may be displayed to a medical coder for the purpose of coding services provided to a patient during an encounter. Patient information, including but not limited to, name, date of birth, gender, enterprise person number (EPN), patient identifier, age, and/or social security number may be provided, such as in area 402. Encounter information, including but not limited to, admit date, discharge date, MRN (medical record number), an encounter identifier, facility, and/or global person indicator (GPI), may be provided in area 404.

As such, a medical coder may view the patient and/or encounter information in areas 402 and/or 404, as well as access any additional information from an associated EHR to assess the encounter and provide accurate billing codes. In this regard, a query may be associated to an EHR identifier, patient identifier, and/or the like so that a user viewing a query may efficiently access the associated EHR. If the medical coder needs additional information in order to identify the appropriate codes, the medical coder initiates a query by selecting a form-based template from drop down 406. The templates may be named such that the query initiator can select an appropriate query based on the scenario. In some embodiments, the selected form-based query template may appear on the same display.

Returning to FIG. 3, as shown by operation 302, the query facilitation apparatus 104 may include means, such as user interface 216, communication interface 218, query configuration circuitry 220, processing circuitry 210 and/or the like, for receiving an indication of a query responder identifying the responder for which the query is intended. In this regard, drop down 408 of FIG. 4 provides a list of selectable users, such as physicians and/or other medical practitioners, to whom the initiator may wish to submit the query (e.g., the query responder). In some examples, the list of available users for query response may be dependent on the particular form-based query selected, such as in an example the template is configured for a practice group or particular physician, for example. In some embodiments, the query responder may be defaulted to a physician as identified as treating the patient during the encounter.

As shown by operation 304, the query facilitation apparatus 104 may include means, such as user interface 216, communication interface 218, query configuration circuitry 220, processing circuitry 210 and/or the like, for receiving a query initiator input to be included in the query. As illustrated in FIG. 4, area 410 provides the query initiator the ability to provide input to the query. In this example embodiment, the query initiator selects an image, such as an x-ray image, associated with the EHR, from area 412. In some embodiments, the query initiator input may include a link to another document. A description of the selected image appears in area 410, and the query initiator may provide free-form text input in area 410 to ask questions regarding the image and/or to clarify information. A link to the image may then be included in the view of the query for the responder such that upon review of the query, the query responder can easily and efficiently access the image. The query initiator may provide input to any number of fields, based on the configuration of the selected form-based template.

In some embodiments, the query initiator may optionally provide aging basis information. For example, aging basis may define when an activity (such as replying to a query) has not been completed in the expected amount of time. Aging can be configured based on a list of dates (for example, Assignment Date, Admission Date, Discharge Date, and Procedure Date). The dates may be populated from the EHR and/or the like. For example, a target deadline may be set as a predetermined amount of time following an assignment date, such as 1 week. If the target deadline elapses and the query responder has not yet responded, the query may be escalated according to various statuses. For example, the status may change from Warning to Delinquent to Pending Suspension. Each level of escalation supports the ability to create a task in a follow-up queue to trigger action by administrative staff, for example. A user may therefore configure the follow-up tasks for each escalation status and for a particular query.

In some examples, fields appearing on a form-based template may be moved, resized, added, and/or deleted as needed by the query initiator so that the form-based template may be customized for a particular use or scenario.

As shown by operation 306, the query facilitation apparatus 104 may include means, such as query configuration circuitry 220, processing circuitry 210 and/or the like, for identifying context data associated with an electronic health record and based on the selected form-based query template. In this regard, the form-based query template is configured to prefill certain data fields from the context data, such as the currently selected patient, encounter, or other data from the EHR. For example, the identified context data may include any data from areas 402 and/or 404 of FIG. 4. Additionally or alternatively, the form-based query template may be configured such that any information available in the EHR is extracted from the EHR and prefilled in the query based on the configuration of the form based template. Said differently, when a form-based template is created or configured, a user identifies fields in the template to be mapped to fields in an EHR. Such functionality may be provided by the template building software such as FormFast®, Adobe®, and/or the like. When the template is used to generate a query instance for a particular patient or encounter, the designated fields as defined by the template are retrieved for the particular EHR (based on a patient identifier and/or encounter identifier, for example).

As shown by operation 308, the query facilitation apparatus 104 may include means, such as user interface 216, communication interface 218, query configuration circuitry 220, processing circuitry 210, memory 214 and/or the like, for storing the query initiator input in association with the selected form based template and the context data associated with the electronic health record. For example, in response to the selection of the save button 414 of FIG. 4, the query input may be stored, along with an indication of the selected form-based query template, such as a template identifier, in the EHR for the particular patient to which the query relates. The query initiator input and indication may, for example, be stored in EHR repository 120 and/or memory 214. Furthermore, a query identifier may be generated, and referenced by a task in the initiator's task list. The query identifier may be used to retrieve metadata describing the query, such as references to the selected form-based template, the initiator input, and/or the like. Additionally or alternatively, once the query is initiated by the query initiator, data loaded into the query, such as fields mapped to the EHR, links to other documents, and/or query initiator input, may be saved in the query as static data. That is, the data may not be inadvertently modified by changing EHRs, but only modified by a user such as the query initiator and/or query responder. Such a configuration may ensure data integrity.

As shown by operation 310, the query facilitation apparatus 104 may include means, such as user interface 216, communication interface 218, query configuration circuitry 220, query routing circuitry 222, processing circuitry 210, memory 214 and/or the like, for causing provision of the query to the query responder such that the query initiator input and the context data associated with the electronic health record is provided in the query.

For example, FIG. 5 is an example display that may be provided to a query responder for indicating a task list of queries. In this particular example, the display is configured to provide incomplete queries. The list may be configured by using the filters and/or search fields in area 502. The listings may provide metadata for each query, including but not limited to, the "assigned to" party (e.g., query responder), assigned date, assignor (e.g., query initiator), form type (e.g., an identifier or description of the form-based template), query type (e.g., description of the particular instance of query that may indicate the usage of the template), facility at which the associated encounter occurred, patient name, MRN, encounter identifier, linked documents, and/or aging status. The query responder may therefore identify particular queries to view, and/or view a queue of incomplete queries, as illustrated in FIG. 5. Upon selecting a specific row of the list, or query, the query may be provided as illustrated in the example display of FIG. 6.

FIG. 6 is an example query that may be provided to a query responder (e.g., physician). The name of the query responder may be prefilled in area 600, based on the selection made by the query initiator, or based on query assignments as provided by the query routing module 222. Area 602 includes data prefilled from the associated EHR and identified based on the configuration of the form-based template. In some examples, as described above, the data from the EHR is loaded upon initiation of the query and saved as static data in the query. As another example, some data from the EHR may be re-loaded upon viewing of the query by the query responder. For example, if data from the EHR changes after the query is initiated and before the query is viewed by the responder, the updated information may be populated into the query such that the query responder views the most recent data.

Area 604 provides the query initiator input, which in this scenario a question is posed by the query initiator for the physician. In some examples, although not illustrated in FIG. 6, the query may include a link to linked documents, such as those linked by the query initiator such that the query responder may easily access the document. The document may then be retrieved from the associated EHR, for example.

As shown by operation 312, the query facilitation apparatus 104 may include means, such as user interface 216, communication interface 218, query configuration circuitry 220, processing circuitry 210 and/or the like, for receiving query responder input from the query responder. For example, areas 606 and 608 are configured for user input. The exclamation point symbol 610 indicates the respective field is required. Other fields, such as 608, may be configured to be optional. In some examples, other visual indications may be provided to distinguish required and optional fields, such as highlighting. In some embodiments the query responder must provide input to the required fields to respond to or complete the query.

In this regard, in some embodiments, the query facilitation apparatus 104 may include means, such as query configuration circuitry 220, processor 212, user interface 216, communication interface 218, and/or the like, for receiving an indication of a plurality of query responder inputs fields and respective requirement indicators. While configuring a form-based template, for example, a user may indicate which fields are to be filled by a query responder. A field may have an associated requirement indicator indicating whether the field is required or optional. The query configuration module 220 may therefore enforce that the required fields are filled by the query responder prior to completion. In an instance there are no required query responder input fields, query configuration module 220 may enforce that at least one query responder input is made to complete the query, thus ensuring that some additional information or query response is provided to the query initiator.

As shown by operation 314, the query facilitation apparatus 104 may include means, such as user interface 216, communication interface 218, query configuration circuitry 220, processing circuitry 210, memory 214, and/or the like, for storing a completed query in association with the EHR. In this regard, the completed query including the query responder's input, may be stored in association with the EHR. The stored completed query may therefore be considered a "snapshot" of the query upon completion such that the fields loaded into the query, such as from the EHR, or manually by the query initiator or responder are saved so as to maintain data integrity. Therefore, once a query is completed by a query responder, the fields in the query should not update to coincide with subsequent changes to an EHR. In this regard, the completed query may be stored on memory 214 and/or the EHR as a static document.

In some instances the query routing module 222 may initiate a communication to the query initiator that the query is complete. In some instances, the query may be routed to a work queue of the query initiator such that the query initiator may complete the associated coding task(s).

In some embodiments, before a query responder completes a query, the query initiator may have the authority to assign the query to a different user. In this regard, the query facilitation apparatus 104 may include means, such as user interface 216, communication interface 218, query routing circuitry 222, processing circuitry 210, and/or the like, for receiving an indication to redirect the query to a different query responder. In this regard, the query initiator may access incomplete queries, and select to change the query responder from one user to another. The query routing circuitry 222 may then unassign the query from the queue of the previous query responder and assign it to a different query responder such that the newly appointed responder can access the query in their work queue or task list.

According to example embodiments, the automated routing of queries from initiators to responders streamlines the process of gathering additional information needed for a query initiator to complete coding tasks. The customization provided by the form-based query enables organizations to provide new, specialized templates as workflows, processes, and/or billing processes change. Fields within a new form-based template may be configured to be loaded from an EHR, configured by the user as query initiator input, and/or query responder input. Furthermore, each query initiator input and/or query responder input may be configured by the user to be required or optional. A supervisor and/or team leader of medical coders, may for example, identify areas of weakness in their processes, or common insufficient information from physicians, and generate new form-based queries on the fly to alleviate such issues. Therefore, subsequent web development to HIS 101 may not be needed to introduce the new form-based templates. Embodiments provided herein may be configured to receive new form-based query templates such that the facilitation of the query initiation and response may evolve along with the organization.

Furthermore, numerous technical advantages are provided, including the conservation of associated memory capacity otherwise utilized to store large volumes of documents such as emails, and written requests, as well as separate responses and/or copies of images and/or other document referred to for such requests. Embodiments provided herein reduce the amount of data and documents stored due to the reuse of templates, and linking of data from the EHR to fields in the form-based templates. Embodiments provided herein enable query initiators to manage their coding assignments in a more expeditious and efficient manner. Similarly, query responders may quickly access queries and the relevant information to efficiently respond with the needed information. Therefore, an additional technical advantage may include the conservation of processing resources of a health information system by avoiding and/or reducing repeated follow-up and access to a system to obtain the requested information. Therefore, embodiments provided herein provide improvements to existing health information systems.

FIG. 3 illustrates operations of a method, apparatus, and computer program product according to some example embodiments. It will be understood that each operation of the flowcharts or diagrams, and combinations of operations in the flowcharts or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, query facilitation apparatus 104) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, query facilitation apparatus 104, and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method executed by a processor of a query facilitation apparatus for facilitating query initiation and query response, the method comprising:
   receiving an indication of a selection of a form-based template for generating a query from a user terminal operated by a query initiator, the user terminal is in network communication with the query facilitation apparatus, wherein the query is a request for coding information for a patient encounter of a patient at a healthcare facility;
   receiving an indication of a query responder for which the query is intended from the user terminal;
   receiving input to be included in the query from the user terminal, wherein the user terminal receives the input from the query initiator, wherein the input facilitates completion of the query by the query responder;
   identifying context data associated with an electronic health record of the patient stored in a health information system based on the form-based template;
   receiving an aging basis for the query from the user terminal, wherein the aging basis defines an expected amount of time for responding to the query, wherein the aging basis is configured to cause a second user terminal operated by the query responder to present at least one alert to the query responder when the expected amount of time for responding to the query is exceeded, the second user terminal is in network communication with the query facilitation apparatus;
   generating the query based upon the input, the form-based template, the context data, and the aging basis;
   causing the query to be stored in association with the electronic health record in the health information system; and
   causing the query to be transmitted to the second user terminal operated by the query responder, wherein the second user terminal presents the query to the query responder on a display of the second user terminal.

2. The method of claim 1, further comprising:
   receiving a query response from the second user terminal; and
   storing the query response in association with the electronic health record.

3. The method of claim 1, further comprising:
   receiving an indication of a plurality of query responder input fields in the query and respective requirement indicators for each of the plurality of query responder input fields from the user terminal;
   in an instance there are no required query responder input fields in the plurality of query responder input fields, requiring at least one query responder input field in the plurality of query responder input fields to be made to complete the query; and
   in an instance there are required query responder input fields in the plurality of query responder input fields, requiring all required query responder input fields in the plurality of query responder input fields to be made to complete the query.

4. The method of claim 1, further comprising:
   receiving an indication of a different query responder to which the query is to be redirected; and
   causing the query to be transmitted to a third user terminal operated by the different query responder, the third user terminal is in network communication with the query facilitation apparatus.

5. The method of claim 1, further comprising:
   receiving an indication of a selection of a second form-based template from the user terminal, wherein the second form-based template includes a plurality of query initiator fields and a plurality of query responder fields; and
   receiving an indication from the user terminal as to which fields in the plurality of query initiator fields and the plurality of query responder fields are optional or required.

6. The method of claim 1, further comprising:
   receiving an indication from the user terminal to link a document to the query; and
   in response to the indication from the user terminal to link the document to the query, causing a link to the document to be included in the query.

7. The method of claim 1, wherein the context data comprises:
   a name of the patient;
   an age of the patient;
   a gender of the patient; and
   a date of the patient encounter at the healthcare facility.

8. A query facilitation apparatus for facilitating query initiation and query response, the query facilitation apparatus comprising processing circuitry configured to cause a processor of the query facilitation apparatus to perform at least:
   receiving an indication of a selection of a form-based template for generating a query from a user terminal operated by a query initiator, the user terminal is in network communication with the query facilitation apparatus, wherein the query is a request for coding information for a patient encounter of a patient at a healthcare facility;
   receiving an indication of a query responder for which the query is intended from the user terminal;
   receiving input to be included in the query from the user terminal, wherein the user terminal receives the input from the query initiator, wherein the input facilitates completion of the query by the query responder;
   identifying context data associated with an electronic health record of the patient stored in a health information system based on the form-based template;
   receiving an aging basis for the query from the user terminal, wherein the aging basis defines an expected amount of time for responding to the query, wherein the aging basis is configured to cause a second user terminal operated by the query responder to present at least one alert to the query responder when the expected amount of time for responding to the query is exceeded, the second user terminal is in network communication with the query facilitation apparatus;

generating the query based upon the input, the form-based template, the context data, and the aging basis;

causing the query to be stored in association with the electronic health record in the health information system; and causing the query to be transmitted to the second user terminal operated by the query responder, wherein the second user terminal presents the query to the query responder on a display of the second user terminal.

9. The query facilitation apparatus of claim 8, wherein the processing circuitry is further configured to cause the query facilitation apparatus to perform at least:

receiving a query response from the second user terminal; and storing the query response in association with the electronic health record.

10. The query facilitation apparatus of claim 8, wherein the processing circuitry is further configured to cause the query facilitation apparatus to perform at least:

receiving an indication of a plurality of query responder input fields in the query and respective requirement indicators for each of the plurality of query responder input fields from the user terminal;

in an instance there are no required query responder input fields in the plurality of query responder input fields, requiring at least one query responder input field in the plurality of query responder input fields to be made to complete the query; and in an instance there are required query responder input fields in the plurality of query responder input fields, requiring all required query responder input fields in the plurality of query responder input fields to be made to complete the query.

11. The query facilitation apparatus of claim 8, wherein the processing circuitry is further configured to cause the query facilitation apparatus to perform at least:

receiving an indication of a different query responder to which the query is to be redirected; and causing the query to be transmitted to a third user terminal operated by the different query responder, the third user terminal is in network communication with the query facilitation apparatus.

12. The query facilitation apparatus of claim 8, wherein the processing circuitry is further configured to cause the query facilitation apparatus to perform at least:

receiving an indication of a selection of a second form-based template from the user terminal, wherein the second form-based template includes a plurality of query initiator fields and a plurality of query responder fields; and receiving an indication from the user terminal as to which fields in a plurality of query initiator fields and the plurality of query responder fields are optional or required.

13. The query facilitation apparatus of claim 8, wherein the processing circuitry is further configured to cause the query facilitation apparatus to perform at least:

receiving an indication from the user terminal to link a document to the query; and in response to the indication from the user terminal to link the document to the query, causing a link to the document to be included in the query.

14. A computer program product for facilitating query initiation and query response, the computer program product comprising at least one non-transitory computer readable medium having computer-readable program instructions stored therein, the computer-readable program instructions comprising instructions, which when performed by a processor of a query facilitation apparatus, are configured to cause the query facilitation apparatus to perform at least:

receiving an indication of a selection of a form-based template for generating a query from a user terminal operated by a query initiator, the user terminal is in network communication with the query facilitation apparatus, wherein the query is a request for coding information for a patient encounter of a patient at a healthcare facility;

receiving an indication of a query responder for which the query is intended from the user terminal;

receiving input to be included in the query from the user terminal, wherein the user terminal receives the input from the query initiator, wherein the input facilitates completion of the query by the query responder;

identifying context data associated with an electronic health record of the patient stored in a health information system based on the form-based template;

receiving an aging basis for the query from the user terminal, wherein the aging basis defines an expected amount of time for responding to the query, wherein the aging basis is configured to cause a second user terminal operated by the query responder to present at least one alert to the query responder when the expected amount of time for responding to the query is exceeded, the second user terminal is in network communication with the query facilitation apparatus;

generating the query based upon the input, the form-based template, the context data, and the aging basis;

causing the query to be stored in association with the electronic health record in the health information system; and causing the query to be transmitted to the second user terminal operated by the query responder, wherein the second user terminal presents the query to the query responder on a display of the second user terminal.

15. The computer program product of claim 14, wherein the computer-readable program instructions further comprise instructions to cause the query facilitation apparatus to perform at least:

receiving a query response from the second user terminal; and storing the query response in association with the electronic health record.

16. The computer program product of claim 14, wherein the computer-readable program instructions further comprise instructions to cause the query facilitation apparatus to perform at least:

receiving an indication of a plurality of query responder input fields in the query and respective requirement indicators for each of the plurality of query responder input fields from the user terminal;

in an instance there are no required query responder input fields in the plurality of query responder input fields, requiring at least one query responder input field in the plurality of query responder input fields to be made to complete the query; and in an instance there are required query responder input fields in the plurality of query responder input fields, requiring all required query responder input fields in the plurality of query responder input fields to be made to complete the query.

17. The computer program product of claim 14, wherein the computer-readable program instructions further comprise instructions to cause the query facilitation apparatus to perform at least:

receiving an indication of a different query responder to which the query is to be redirected; and causing the query to be transmitted to a third user terminal operated by the different query responder, the third user terminal is in network communication with the query facilitation apparatus.

18. The computer program product of claim 14, wherein the computer-readable program instructions further comprise instructions to cause the query facilitation apparatus to perform at least:

receiving an indication of a selection of a second form-based template from the user terminal, wherein the second form-based template includes a plurality of query initiator fields and a plurality of query responder fields; and receiving an indication from the user terminal as to which fields in the plurality of query initiator fields and the plurality of query responder fields are optional or required.

19. The computer program product of claim 14, wherein the computer-readable program instructions further comprise instructions to cause the query facilitation apparatus to perform at least:

receiving an indication from the user terminal to link a document to the query; and in response to the indication from the user terminal to link the document to the query, causing a link to the document to be included in the query.

20. The computer program product of claim 14, wherein the context data comprises:

a name of the patient;

an age of the patient;

a gender of the patient; and a date of the patient encounter at the healthcare facility.

* * * * *